US009023986B2

(12) United States Patent
Danho et al.

(10) Patent No.: US 9,023,986 B2
(45) Date of Patent: May 5, 2015

(54) GLUCOSE-DEPENDENT INSULINOTROPIC PEPTIDE ANALOGS

(75) Inventors: Waleed Danho, Del Mar, CA (US);
George Ehrlich, Bronx, NY (US);
Wajiha Khan, East Hanover, NJ (US);
Joseph Swistok, Nutley, NJ (US);
Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 497 days.

(21) Appl. No.: 13/274,372

(22) Filed: Oct. 17, 2011

(65) Prior Publication Data

US 2012/0101037 A1 Apr. 26, 2012

Related U.S. Application Data

(60) Provisional application No. 61/406,186, filed on Oct. 25, 2010.

(51) Int. Cl.
| | | |
|---|---|---|
| *C07K 14/00* | (2006.01) | |
| *C07K 14/575* | (2006.01) | |
| *A61K 38/22* | (2006.01) | |
| *C07K 14/605* | (2006.01) | |
| *A61K 38/00* | (2006.01) | |

(52) U.S. Cl.
CPC .............. *C07K 14/605* (2013.01); *A61K 38/00* (2013.01); *A61K 38/22* (2013.01)

(58) Field of Classification Search
USPC .......................................... 530/324; 514/6.7
See application file for complete search history.

(56) References Cited

U.S. PATENT DOCUMENTS

| | | | |
|---|---|---|---|
| 6,921,748 | B1 | 7/2005 | O'Harte et al. |
| 7,091,183 | B1 | 8/2006 | Wolfe et al. |
| 7,326,688 | B2 | 2/2008 | O'Harte et al. |
| 7,576,050 | B2 | 8/2009 | Greig et al. |
| 2002/0151495 | A1 | 10/2002 | Wolfe et al. |
| 2004/0029805 | A1 | 2/2004 | Wolfe et al. |
| 2006/0293232 | A1 | 12/2006 | Levy et al. |
| 2007/0167363 | A1 | 7/2007 | Wolfe et al. |
| 2007/0167374 | A1 | 7/2007 | Wolfe et al. |
| 2008/0125371 | A1 | 5/2008 | Wolfe et al. |
| 2008/0182795 | A1 | 7/2008 | Wolfe et al. |
| 2008/0312157 | A1 | 12/2008 | Levy et al. |
| 2009/0036364 | A1 | 2/2009 | Levy et al. |
| 2009/0186817 | A1 | 7/2009 | Ghosh et al. |
| 2009/0253625 | A1 | 10/2009 | Greig et al. |
| 2009/0286723 | A1 | 11/2009 | Levy et al. |
| 2010/0041098 | A1 | 2/2010 | Steward et al. |

FOREIGN PATENT DOCUMENTS

| | | |
|---|---|---|
| EP | 1171465 | 1/2002 |
| WO | 00/58360 | 10/2000 |
| WO | 03/082898 | 10/2003 |
| WO | 2005/082928 | 9/2005 |
| WO | 2006/086769 | 8/2006 |
| WO | 2006/121904 | 11/2006 |
| WO | 2007/022123 | 2/2007 |
| WO | 2007/028632 | 3/2007 |
| WO | 2007/028633 | 3/2007 |
| WO | 2007/109354 | 9/2007 |
| WO | 2008/021560 | 2/2008 |
| WO | 2008/076933 | 6/2008 |
| WO | 2009/030498 | 3/2009 |
| WO | 2009/042922 | 4/2009 |
| WO | 2009/099763 | 8/2009 |
| WO | 2010/011439 | 1/2010 |
| WO | 2010/012495 | 2/2010 |
| WO | 2010/016935 | 2/2010 |
| WO | 2010/016936 | 2/2010 |
| WO | 2010/016938 | 2/2010 |
| WO | 2010/016940 | 2/2010 |
| WO | 2010/016944 | 2/2010 |
| WO | 2010/033207 | 3/2010 |
| WO | 2010/033220 | 3/2010 |
| WO | 2010/033240 | 3/2010 |
| WO | 2010/0718007 | 6/2010 |

OTHER PUBLICATIONS

"Acta Chemica Scandinavica, Series B: Organic Chemistry & Biochemistry" B41(7):494-498 ( 1987).
Hinke et al., "Biochimica et Biophysica Acta, Protein Structure & Molecular Enzymology" 1547:143-155 ( 2001).
Salhanick et al., "Bioorganic & Medicinal Chemistry Letters" 15:4114-4117 ( 2005).
Gaul et al., "Biochemical Pharmacology" 75:2325-2333 ( 2008).
McCLean et al., "British Journal of Pharmacology" 155:690-701 ( 2008).
Irwin et al., "Journal of Medicinal Chemistry" 48:1244-1250 ( 2005).
Hinke et al., "Biological Chemistry" 384:403-407 ( 2003).
Gault et al., "Biochemical Journal" 367:913-920 ( 2002)
Kerr et al., "Peptides" 30:219-225 ( 2009).
Hinke et al., "Life Sciences" 75:1857-1870 ( 2004).
"International Search Report PCT/EP2011/068385 mailed Feb. 24, 2012".
Kuhn et al., "Advances in Experimental Medicine & Biology" 477:187-195 ( 2000).
Irwin et al., "Biochemical Pharmacology" 72:719-728 ( 2006).
Alana et al., "Biochemical & Biophysical Research Communications" 325:281-286 ( 2004).
Maletti et al., "Diabetes" 36:1336-1340 ( 1987).
Chapter et al., "Pharmacology & Therapeutics" 125(1):39-54 ( 2010).
Ohare et al., "Diabetologia" 45:1281-1291 ( 2002).
Werle et al., "Amino Acids: The Forum for Amino Acid & Protein Research" 30(4):351-367 (2006).

*Primary Examiner* — David Lukton

(57) ABSTRACT

The present invention provides compounds which are analogs of glucose-dependent insulinotropic polypeptide (GIP) and pharmaceutically acceptable salts of such compounds. These compounds have activity as agonists of GIP receptor.

41 Claims, 9 Drawing Sheets

GLUCOSE-DEPENDENT INSULINOTROPIC PEPTIDE ANALOGS

PRIORITY TO RELATED APPLICATION(S)

This application claims the benefit of U.S. Provisional Application No. 61/406,186, filed Oct. 25, 2010. The entire contents of the above-identified application is hereby incorporated by reference.

FIELD OF THE INVENTION

The present invention relates to analogs of glucose-dependent insulinotropic polypeptide and methods of using the same. The compounds of the invention, or pharmaceutically acceptable salts thereof, may be used for treating metabolic diseases and disorders including, for example, obesity, diabetes, metabolic syndrome, insulin resistance, dyslipidemia, impaired fasting glucose, and impaired glucose tolerance.

BACKGROUND OF THE INVENTION

Insulin is a hormone that plays a major role in the regulation of glucose metabolism by stimulating the uptake of glucose in liver, muscle, and fat tissue. Glucose is stored in such tissue and metabolized for energy. Failure to produce insulin, dysregulation of insulin, or resistance to insulin lead to metabolic diseases and disorders, for example, diabetes.

Glucose-dependent insulinotropic polypeptide (GIP) is a 42-residue peptide that is secreted by the upper gut. Both carbohydrates and lipids stimulate the secretion of GIP. Along with GLP-1, GIP is an incretin, meaning that it has the ability to stimulate the release of insulin. The effects of GIP are mediated by its binding to GIP receptor (GIPR). It is believed that this binding stimulates cAMP which facilitates glucose stimulated insulin release in the pancreatic β-cells.

In vivo, native GIP is rapidly degraded by the enzyme dipeptidyl peptidase IV (DPPIV) which removes the two N-terminal residues, Tyr-Ala. The half life of native GIP in vivo is about 2 to 7 minutes depending on species. The metabolite (GIP 3-42) does not activate GIPR and, in fact, serves as an antagonist of GIPR. In addition, the metabolite is readily cleared in humans. As such, the effectiveness of native GIP as a therapeutic is limited.

The present invention relates to the development of truncated GIP (1-42) analogs which retain the potency of GIP and its ability to bind GIPR, serving as an agonist thereof, while having improved plasma stability and increased half life in vivo as compared with native GIP.

SUMMARY OF THE INVENTION

The present invention provides compounds which are analogs of glucose-dependent insulinotropic polypeptide (GIP) and pharmaceutically acceptable salts of such compounds. In certain embodiments, the compounds are compounds of formula (I):

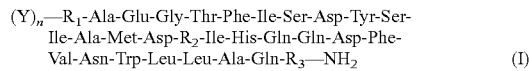

(Y)$_n$—R$_1$-Ala-Glu-Gly-Thr-Phe-Ile-Ser-Asp-Tyr-Ser-Ile-Ala-Met-Asp-R$_2$-Ile-His-Gln-Gln-Asp-Phe-Val-Asn-Trp-Leu-Leu-Ala-Gln-R$_3$—NH$_2$  (I)

wherein:
R$_1$ is selected from the group consisting of: (D)Tyr; DesNH$_2$-Tyr; (D)Phe; DesNH$_2$-Phe; (D)Trp; (D)3Pya; 2-Cl-(D)Phe; 3-Cl-(D)Phe; 4-Cl-(D)Phe; 2-F-(D)Phe; 3-F-(D)Phe; 3,5-DiF(D)Phe; and 3,4,5-TriF(D)Phe;
R$_2$ is Lys or Ala;
R$_3$ is Lys or PEGylated Lys;
Y is acyl;
n is 1 when R$_1$ is (D)Tyr; (D)Phe; (D)Trp; (D)3Pya; 2-Cl-(D)Phe; 3-Cl-(D)Phe; 4-Cl-(D)Phe; 2-F-(D)Phe; 3-F-(D)Phe; 3,5-DiF(D)Phe; or 3,4,5-TriF(D)Phe; and
n is 0 when R$_1$ is DesNH$_2$-Tyr or DesNH$_2$-Phe;
or a pharmaceutically-acceptable salt thereof.

These compounds have activity as agonists of GIP receptor.

The invention relates also to a pharmaceutical composition comprising a therapeutically effective amount of a compound as described above, or a pharmaceutically acceptable salt thereof, and a pharmaceutically acceptable carrier.

The invention relates further to the use of the compound as described above, or a pharmaceutically acceptable salt thereof, in the manufacture of a medicament.

In addition, the invention relates to a method of treating a metabolic disease or disorder, for example, obesity, diabetes, metabolic syndrome, insulin resistance, dyslipidemia, impaired fasting glucose, and impaired glucose tolerance, comprising administering to a patient in need of said treatment an effective amount of a compound as described above, or a pharmaceutically acceptable salt thereof.

Further, the invention relates to a method of agonizing glucose-dependent insulinotropic polypeptide receptor (GIPR) in an individual comprising administering to the individual the compound as described above, or a pharmaceutically acceptable salt thereof, in an amount effective in agonizing GIPR.

DETAILED DESCRIPTION OF THE INVENTION

Figure 1:
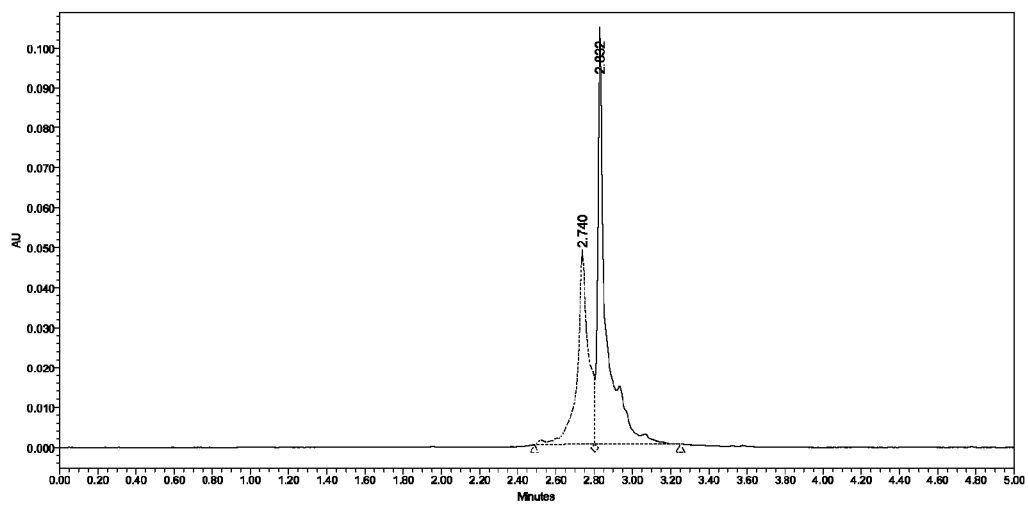
FIG. 1 shows an RP-HPLC chromatogram of a reaction mixture containing the compound of Example 20.

All peptide sequences mentioned herein are written according to the usual convention whereby the N-terminal amino acid is on the left and the C-terminal amino acid is on the right, unless noted otherwise. A short line between two amino acid residues indicates a peptide bond. Where the amino acid has isomeric forms, it is the L form of the amino acid that is represented unless otherwise expressly indicated. Unless specifically noted, the residues are not PEGylated.

For convenience in describing this invention, the conventional and nonconventional abbreviations for the various amino acids residues are used. These abbreviations are familiar to those skilled in the art, but for clarity are listed below:
Asp=D=Aspartic Acid; Ala=A=Alanine; Arg=R=Arginine; Asn=N=Asparagine; Gly=G=Glycine; Glu=E=Glutamic Acid; Gln=Q=Glutamine; His=H=Histidine;

Ile=I=Isoleucine; Leu=L=Leucine; Lys=K=Lysine; Met=M=Methionine; Phe=F=Phenylalanine; Pro=P=Proline; Ser=S=Serine; Thr=T=Threonine; Trp=W=Tryptophan; Tyr=Y=Tyrosine; and Val=V=Valine.

Also for convenience, and readily known to one skilled in the art, the following abbreviations or symbols are used to represent the moieties, reagents and the like used in this invention:
(D)Tyr D-tyrosine
DesNH$_2$-Tyr desaminotyrosine
(D)Phe D-phenylalanine
DesNH$_2$-Phe desaminophenylalanine
(D)Trp D-tryptophan
(D)3Pya D-3-pyridylalanine
2-Cl-(D)Phe D-2-chlorophenylalanine
3-Cl-(D)Phe D-3-chlorophenylalanine
4-Cl-(D)Phe D-4-chlorophenylalanine
2-F-(D)Phe D-2-fluorophenylalanine
3-F(D)Phe D-3-fluorophenylalanine
3,5-DiF-(D)Phe D-3,5-difluorophenylalanine
3,4,5-TriF-(D)Phe D-3,4,5-trifluorophenylalanine
SSA succinimidyl succinamide
PEG polyethylene glycol
PEG$_m$ (methoxy)polyethylene glycol
PEG$_m$(12,000) (methoxy)polyethylene glycol having a molecular weight of about 12 kD
PEG$_m$(20,000) (methoxy)polyethylene glycol having a molecular weight of about 20 kD
PEG$_m$(30,000) (methoxy)polyethylene glycol having a molecular weight of about 30 kD
Fmoc 9-fluorenylmethyloxycarbonyl
DMF dimethylformamide
DIPEA N,N-diisopropylethylamine
TFA trifluoroacetic acid
HOBT N-hydroxybenzotriazole
BOP benzotriazol-1-yloxy-tris-(dimethylamino)phosphonium-hexafluorophosphate
HBTU 2-(1H-benzotriazole-1-yl)-1,1,3,3-tetramethyluronium-hexafluorophosphate
NMP N-methyl-pyrrolidone
FAB-MS fast atom bombardment mass spectrometry
ES-MS electro spray mass spectrometry As used herein, "PEG moiety" refers to polyethylene glycol (PEG) or a derivative thereof, for example (methoxy) polyethylene glycol (PEG$_m$).

As used herein, "PEGylated peptide" refers to a peptide wherein at least one amino acid residue, for example, lysine, has been conjugated with a PEG moiety. By "conjugated", it is meant that the PEG moiety is either directly linked to said residue or is linked to the residue via a spacer moiety, for example a cross-linking agent. When said conjugation is at a lysine residue, that lysine residue is referred to herein as "PEGylated Lys". A peptide that is conjugated to only one PEG moiety is said to be "mono-PEGylated".

As used herein, "Lys-PEG" and "Lys-PEG$_m$" refer respectively to lysine residues which have been conjugated with PEG and PEG$_m$. "Lys(epsilon-SSA-PEG$_m$)" refers to a lysine residue wherein the epsilon-amino group has been cross-linked with PEG$_m$ using a suitably functionalized SSA. "Lys (epsilon-SSA-PEG$_m$(12,000))" refers to a lysine residue wherein the epsilon-amino group has been cross-linked with PEG$_m$(12,000) using a suitably-functionalized SSA; "Lys (epsilon-SSA-PEG$_m$(20,000))" refers to a lysine residue wherein the epsilon-amino group has been cross-linked with PEG$_m$(20,000) using a suitably-functionalized SSA; and "Lys(epsilon-SSA-PEG$_m$(30,000))" refers to a lysine residue wherein the epsilon-amino group has been cross-linked with PEG$_m$(30,000) using a suitably-functionalized SSA.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, trifluoroacetic acid, oxalic, and p-toluenesulfonic acids and the like. In an embodiment, the acids are fumaric, hydrochloric, hydrobromic, phosphoric, succinic, sulfuric, trifluoroacetic, or methanesulfonic acids. Acceptable base salts include alkali metal (e.g. sodium, potassium), alkaline earth metal (e.g. calcium, magnesium) and aluminum salts.

The term "pharmaceutical formulation" refers to a preparation which is in such form as to permit the biological activity of an active ingredient contained therein to be effective, and which contains no additional components which are unacceptably toxic to a subject to which the formulation would be administered.

As used herein, a "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The present invention provides compounds which are analogs of glucose-dependent insulinotropic polypeptide (GIP) and pharmaceutically acceptable salts of such compounds. These compounds have activity as agonists of GIP receptor.

In certain embodiments, the compounds are compounds of formula (I):

(Y)$_n$—R$_1$-Ala-Glu-Gly-Thr-Phe-Ile-Ser-Asp-Tyr-Ser-Ile-Ala-Met-Asp-R$_2$-Ile-His-Gln-Gln-Asp-Phe-Val-Asn-Trp-Leu-Leu-Ala-Gln-R$_3$—NH$_2$ (I)

wherein:
R$_1$ is selected from the group consisting of: (D)Tyr; DesNH$_2$-Tyr; (D)Phe; DesNH$_2$-Phe; (D)Trp; (D)3Pya; 2-Cl-(D) Phe; 3-Cl-(D)Phe; 4-Cl-(D)Phe; 2-F-(D)Phe; 3-F-(D)Phe; 3,5-DiF(D)Phe; and 3,4,5-TriF(D)Phe;
R$_2$ is Lys or Ala;
R$_3$ is Lys or PEGylated Lys;
Y is acyl;
n is 1 when R$_1$ is (D)Tyr; (D)Phe; (D)Trp; (D)3Pya; 2-Cl-(D) Phe; 3-Cl-(D)Phe; 4-Cl-(D)Phe; 2-F-(D)Phe; 3-F-(D)Phe; 3,5-DiF-(D)Phe; or 3,4,5-TriF(D)Phe; and
n is 0 when R$_1$ is DesNH$_2$-Tyr or DesNH$_2$-Phe;
or a pharmaceutically-acceptable salt thereof.

The compounds of the invention, or pharmaceutically acceptable salts thereof, may be used for treating metabolic diseases and disorders. Such metabolic diseases and disorders include, for example, obesity, diabetes, preferably type 2 diabetes, metabolic syndrome, insulin resistance, dyslipidemia, impaired fasting glucose, and impaired glucose tolerance.

In an embodiment of the present invention, $R_1$ is selected from the group consisting of: (D)Tyr or DesNH$_2$-Tyr.

In an embodiment of the present invention, $R_1$ is (D)Tyr.

In an embodiment of the present invention, $R_1$ is selected from the group consisting of: (D)Phe; DesNH$_2$-Phe; 2-Cl-(D)Phe; 3-Cl-(D)Phe; 4-Cl-(D)Phe; 2-F-(D)Phe; 3-F-(D)Phe; 3,5-DiF-(D)Phe; and 3,4,5-TriF-(D)Phe.

In an embodiment of the present invention, $R_1$ is (D)Trp.

In an embodiment of the present invention, $R_1$ is (D)3Pya.

In an embodiment of the present invention, $R_2$ is Lys.

In an embodiment of the present invention, $R_2$ is Ala.

In an embodiment of the present invention, $R_3$ is Lys.

In an embodiment of the present invention, $R_3$ is PEGylated Lys.

In an embodiment of the present invention, $R_3$ is Lys-PEG.

In an embodiment of the present invention, $R_3$ is Lys-PEG$_m$.

In an embodiment of the present invention, $R_3$ is PEGylated Lys wherein the PEG moiety has a molecular weight of from about 5,000 to about 40,000 Daltons.

In an embodiment of the present invention, $R_3$ is PEGylated Lys wherein the PEG moiety has a molecular weight of from about 10,000 to about 30,000 Daltons.

In an embodiment of the present invention, $R_3$ is PEGylated Lys wherein the PEG moiety has a molecular weight of from about 15,000 to about 25,000 Daltons.

In an embodiment of the present invention, $R_3$ is PEGylated Lys wherein the PEG moiety has a molecular weight of about 20,000 Daltons.

In an embodiment of the present invention, $R_3$ is Lys-PEG$_m$ wherein the PEG$_m$ has a molecular weight of from about 5,000 to about 40,000 Daltons.

In an embodiment of the present invention, $R_3$ is Lys-PEG$_m$ wherein the PEG$_m$ has a molecular weight of from about 10,000 to about 30,000 Daltons.

In an embodiment of the present invention, $R_3$ is Lys-PEG$_m$ wherein the PEG$_m$ has a molecular weight of from about 15,000 to about 25,000 Daltons.

In an embodiment of the present invention, $R_3$ is Lys-PEG$_m$ wherein the PEG$_m$ has a molecular weight of about 20,000 Daltons.

In an embodiment of the present invention, $R_3$ is Lys (epsilon-SSA-PEG$_m$).

In an embodiment of the present invention, $R_3$ is Lys (epsilon-SSA-PEG$_m$) wherein said PEG$_m$ has a molecular weight of from about 5,000 to about 40,000 Daltons.

In an embodiment of the present invention, $R_3$ is selected from the group consisting of: Lys(epsilon-SSA-PEG$_m$(12,000)), Lys(epsilon-SSA-PEG$_m$(20,000)), and Lys(epsilon-SSA-PEG$_m$(30,000)).

In an embodiment of the present invention, $R_3$ is Lys(epsilon-SSA-PEG$_m$(20,000)).

In an embodiment of the present invention, $R_1$ is (D)Tyr or DesNH$_2$-Tyr and $R_2$ is Ala.

In an embodiment of the present invention, $R_1$ is (D)Tyr or DesNH$_2$-Tyr, $R_2$ is Ala, and $R_3$ is PEGylated Lys.

In an embodiment of the present invention, $R_1$ is (D)Tyr or DesNH$_2$-Tyr, $R_2$ is Ala, and $R_3$ is PEGylated Lys wherein the PEG moiety has a molecular weight of from about 5,000 to about 40,000 Daltons.

In an embodiment of the present invention, $R_1$ is (D)Tyr or DesNH$_2$-Tyr, $R_2$ is Ala, and $R_3$ is PEGylated Lys wherein the PEG moiety has a molecular weight of from about 10,000 to about 30,000 Daltons.

In an embodiment of the present invention, $R_1$ is (D)Tyr or DesNH$_2$-Tyr, $R_2$ is Ala, and $R_3$ is PEGylated Lys wherein the PEG moiety has a molecular weight of from about 15,000 to about 25,000 Daltons.

In an embodiment of the present invention, $R_1$ is (D)Tyr or DesNH$_2$-Tyr, $R_2$ is Ala, and $R_3$ is PEGylated Lys wherein the PEG moiety has a molecular weight of about 20,000 Daltons.

In an embodiment of the present invention, $R_1$ is (D)Tyr or DesNH$_2$-Tyr, $R_2$ is Ala, and $R_3$ is Lys-PEG$_m$ wherein the PEG$_m$ has a molecular weight of from about 5,000 to about 40,000 Daltons.

In an embodiment of the present invention, $R_1$ is (D)Tyr or DesNH$_2$-Tyr, $R_2$ is Ala, and $R_3$ is Lys-PEG$_m$ wherein the PEG$_m$ has a molecular weight of from about 10,000 to about 30,000 Daltons.

In an embodiment of the present invention, $R_1$ is (D)Tyr or DesNH$_2$-Tyr, $R_2$ is Ala, and $R_3$ is Lys-PEG$_m$ wherein the PEG$_m$ has a molecular weight of from about 15,000 to about 25,000 Daltons.

In an embodiment of the present invention, $R_1$ is (D)Tyr or DesNH$_2$-Tyr, $R_2$ is Ala, and $R_3$ is Lys-PEG$_m$ wherein the PEG$_m$ has a molecular weight of about 20,000 Daltons.

In an embodiment of the present invention, $R_1$ is (D)Tyr, $R_2$ is Ala, and $R_3$ is Lys-PEG$_m$ wherein the PEG$_m$ has a molecular weight of about 20,000 Daltons.

In an embodiment of the present invention, the compound is selected from the group consisting of:

Ac-(D)Tyr-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 3);

DesNH$_2$-Tyr-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 4);

Ac-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 5);

DesNH$_2$-Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 6);

Ac-(D)Trp-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 7);

Ac-(D)3Pya-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 8);

Ac-2-Cl-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 9);

Ac-3-Cl-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 10);

Ac-4-Cl-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 11);

Ac-2-F-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 12);

Ac-3-F-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 13);

Ac-3,5-DiF-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 14);

Ac-3,4,5-TriF-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 15);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys-NH$_2$ (SEQ ID NO: 16);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(12,000))-NH$_2$ (SEQ ID NO: 17);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(20,000))-NH$_2$ (SEQ ID NO: 18);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(30,000))-NH$_2$ (SEQ ID NO: 19); and pharmaceutically acceptable salts thereof.

In an embodiment of the present invention, the compound is selected from the group consisting of:

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys-NH$_2$ (SEQ ID NO: 16);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(12,000))-NH$_2$ (SEQ ID NO: 17);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(20,000))-NH$_2$ (SEQ ID NO: 18);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(30,000))-NH$_2$ (SEQ ID NO: 19);

and pharmaceutically-acceptable salts thereof.

In an embodiment of the present invention, the compound is:

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys-NH$_2$ (SEQ ID NO: 16) or a pharmaceutically-acceptable salt thereof.

In an embodiment of the present invention, the compound is selected from the group consisting of:

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(12,000))-NH$_2$ (SEQ ID NO: 17);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(20,000))-NH$_2$ (SEQ ID NO: 18);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(30,000))-NH$_2$ (SEQ ID NO: 19);

and pharmaceutically-acceptable salts thereof.

In an embodiment of the present invention, the compound is selected from the group consisting of:

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(20,000))-NH$_2$ (SEQ ID NO: 18);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(30,000))-NH$_2$ (SEQ ID NO: 19);

and pharmaceutically-acceptable salts thereof.

In an embodiment of the present invention, the compound is Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(20,000))-NH$_2$ (SEQ ID NO: 18) or a pharmaceutically-acceptable salt thereof.

The compounds of the present invention may be readily synthesized by any known conventional procedure for the formation of a peptide linkage between amino acids. Such conventional procedures include, for example, any solution phase procedure permitting a condensation between the free alpha amino group of an amino acid or fragment thereof having its carboxyl group and other reactive groups protected and the free primary carboxyl group of another amino acid or fragment thereof having its amino group or other reactive groups protected.

Such conventional procedures for synthesizing the novel compounds of the present invention include, for example, any solid phase peptide synthesis method. In such a method the synthesis of the novel compounds can be carried out by sequentially incorporating the desired amino acid residues one at a time into the growing peptide chain according to the general principles of solid phase methods. Such methods are disclosed in, for example, Merrifield, R. B., J. Amer. Chem. Soc. 85, 2149-2154 (1963); Barany et al., The Peptides, Analysis, Synthesis and Biology, Vol. 2, Gross, E. and Meienhofer, J., Eds. Academic Press 1-284 (1980), which are incorporated herein by reference.

During the synthesis of peptides, it may be desired that certain reactive groups on the amino acid, for example, the alpha-amino group, a hydroxyl group, and/or reactive side chain groups, be protected to prevent a chemical reaction therewith. This may be accomplished, for example, by reacting the reactive group with a protecting group which may later be removed. For example, the alpha amino group of an amino acid or fragment thereof may be protected to prevent a chemical reaction therewith while the carboxyl group of that amino acid or fragment thereof reacts with another amino acid or fragment thereof to form a peptide bond. This may be followed by the selective removal of the alpha amino protecting group to allow a subsequent reaction to take place at that site, for example with the carboxyl group of another amino acid or fragment thereof.

Alpha amino groups may, for example, be protected by a suitable protecting group selected from aromatic urethane-type protecting groups, such as allyloxycarbony, benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropyloxycarbonyl, 9-fluorenylmethyloxycarbonyl (Fmoc) and p-methoxybenzyloxycarbonyl (Moz); and aliphatic urethane-type protecting groups, such as t-butyloxycarbonyl (Boc), diisopropylmethyloxycarbonyl, isopropyloxycarbonyl, and allyloxycarbonyl. In an embodiment, Fmoc is used for alpha amino protection.

Hydroxyl groups (OH) of the amino acids may, for example, be protected by a suitable protecting group selected from benzyl (Bzl), 2,6-dichlorobenzyl (2,6 diCl-Bzl), and tert-butyl (t-Bu). In an embodiment wherein a hydroxyl group of tyrosine, serine, or threonine is intended to be protected, t-Bu may, for example, be used.

Epsilon-amino acid groups may, for example, be protected by a suitable protecting group selected from 2-chloro-benzyloxycarbonyl (2-Cl-Z), 2-bromo-benzyloxycarbonyl (2-Br—Z), allycarbonyl and t-butyloxycarbonyl (Boc). In an embodiment wherein an epsilon-amino group of lysine is intended to be protected, Boc may, for example, be used.

Beta- and gamma-amide groups may, for example, be protected by a suitable protecting group selected from 4-methyltrityl (Mtt), 2,4,6-trimethoxybenzyl (Tmob), 4,4'-dimethoxydityl (Dod), bis-(4-methoxyphenyl)-methyl and Trityl (Trt). In an embodiment wherein an amide group of asparagine or glutamine is intended to be protected, Trt may, for example, be used.

Indole groups may, for example, be protected by a suitable protecting group selected from formyl (For), Mesityl-2-sulfonyl (Mts) and t-butyloxycarbonyl (Boc). In an embodiment wherein the indole group of tryptophan is intended to be protected, Boc may, for example, be used.

Imidazole groups may, for example, be protected by a suitable protecting group selected from Benzyl (Bzl), t-butyloxycarbonyl (Boc), and Trityl (Trt). In an embodiment wherein the imidazole group of histidine is intended to be protected, Trt may, for example, be used.

Solid phase synthesis may be commenced from the C-terminal end of the peptide by coupling a protected alpha-amino acid to a suitable resin. Such a starting material can be prepared by attaching an alpha-amino-protected amino acid by an ester linkage to a p-benzyloxybenzyl alcohol (Wang) resin, or by an amide bond between an Fmoc-Linker, such as p-((R,S)-α-(1-(9H-fluoren-9-yl)-methoxyformamido)-2,4-dimethyloxybenzyl)-phenoxyacetic acid (Rink linker), and a benzhydrylamine (BHA) resin. Preparation of the hydroxymethyl resin is well known in the art. Fmoc-Linker-BHA resin supports are commercially available and generally used when the desired peptide being synthesized has an unsubstituted amide at the C-terminus.

In an embodiment, peptide synthesis is microwave assisted. Microwave assisted peptide synthesis is an attractive method for accelerating the solid phase peptide synthesis. This may be performed using Microwave Peptide Synthesizer, for example a Liberty peptide synthesizer (CEM Corporation, Matthews, N.C.). Microwave assisted peptide synthesis allows for methods to be created that control a reaction at a set temperature for a set amount of time. The synthesizer automatically regulates the amount of power delivered to the reaction to keep the temperature at the set point.

Typically, the amino acids or mimetic are coupled onto the Fmoc-Linker-BHA resin using the Fmoc protected form of amino acid or mimetic, with 2-5 equivalents of amino acid and a suitable coupling reagent. After coupling, the resin may be washed and dried under vacuum. Loading of the amino acid onto the resin may be determined by amino acid analysis of an aliquot of Fmoc-amino acid resin or by determination of Fmoc groups by UV analysis. Any unreacted amino groups may be capped by reacting the resin with acetic anhydride and diisopropylethylamine in methylene chloride.

The resins are carried through several repetitive cycles to add amino acids sequentially. The alpha amino Fmoc protecting groups are removed under basic conditions. Piperidine, piperazine or morpholine (20-40% v/v) in DMF may be used for this purpose. In an embodiment, 20% piperidine in DMF is utilized.

Following the removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. For example, appropriate reagents for such syntheses are benzotriazol-1-yloxy-tri-(dimethylamino) phosphonium hexafluorophosphate (BOP), bromo-tris-pyrrolidino-phosphonium hexafluorophosphate (PyBroP) 2-(1H-benzotriazole-1-yl)-1,1,3,3-tetramethyluronium hexafluorophosphate (HBTU), and diisopropylcarbodiimide (DIC). In an embodiment, the reagent is HBTU or DIC. Other activating agents are described by Barany and Merrifield (in The Peptides, Vol. 2, J. Meienhofer, ed., Academic Press, 1979, pp 1-284). Various reagents such as 1 hydroxybenzotriazole (HOBT), N-hydroxysuccinimide (HOSu) and 3,4-dihydro-3-hydroxy-4-oxo-1,2,3-benzotriazine (HOOBT) may be added to the coupling mixtures in order to optimize the synthetic cycles. In an embodiment, HOBT is added.

Following synthesis of the peptide, the blocking groups may be removed and the peptide cleaved from the resin. For example, the peptide-resins may be treated with 100 µL ethanedithiol, 100 µl dimethylsulfide, 300 µL anisole, and 9.5 mL trifluoroacetic acid, per gram of resin, at room temperature for 180 min. Alternatively, the peptide-resins may be treated with 1.0 mL triisopropyl silane and 9.5 mL trifluoroacetic acid, per gram of resin, at room temperature for 90 min. The resin may then be filtered off and the peptide precipitated by addition of chilled ethyl ether. The precipitates may then be centrifuged and the ether layer decanted.

Purification of the crude peptide may be, for example, performed on a Shimadzu LC-8A system by high performance liquid chromatography (HPLC) on a reverse phase $C_{18}$ Column (50×250 mm, 300 Å, 10 µm). The peptides may be dissolved in a minimum amount of water and acetonitrile and injected on to a column. Gradient elution may be generally started at 2%-70% B over 70 minutes, (buffer A: 0.1% TFA/$H_2O$, buffer B: 0.1% TFA/$CH_3CN$) at a flow rate of 60 ml/min. UV detection set at 220/280 nm. The fractions containing the products may be separated and their purity judged on Shimadzu LC-10AT analytical system using reverse phase Pursuit $C_{18}$ column (4.6×50 mm) at a flow rate of 2.5 ml/min., gradient (2-70%) over 10 min. [buffer A: 0.1% TFA/$H_2O$, buffer B: 0.1% TFA/$CH_3CN$)]. Fractions judged to be of high purity may then be pooled and lyophilized.

As stated above, in certain embodiments, the lysine reside at position 30 of the peptides of the present invention is cross-linked at the epsilon-amino group, for example using SSA, with a PEG moiety. The cross-linking may be performed in solution at basic pH, whereby the cross-linking reagent preferentially reacts with primary amines, such as the epsilon-amine. The resulting PEGylated peptide is covalently conjugated through a stable amide bond. The PEGylated peptide may then be isolated from the reaction mixture by cation/anion exchange chromatography, whereby the choice of exchange resin is generally dependent on the net charge of the conjugate.

The compounds of the present invention can be provided in the form of pharmaceutically acceptable salts. Examples of preferred salts are those formed with pharmaceutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids, such as hydrohalic acids (e.g., hydrochloric acid), sulfuric acid, or phosphoric acid and the like. Any procedure for obtaining a pharmaceutically acceptable salt known to a skilled artisan can be used.

The present invention also relates in part to a method of treating a metabolic disease or disorder, comprising administering to a patient in need of said treatment a therapeutically effective amount of a compound of the present invention, or a pharmaceutically acceptable salt thereof. The metabolic disease or disorder may, for example, be obesity, type 2 diabetes, metabolic syndrome, insulin resistance, dyslipidemia, impaired fasting glucose, or impaired glucose tolerance.

In the practice of the method of the present invention, an effective amount of any one of the compounds of this invention, or a pharmaceutically acceptable salt thereof, or a combination of any of the compounds of this invention, or pharmaceutically acceptable salts thereof, is administered via any of the usual and acceptable methods known in the art, either singly or in combination. Administration can be, for example, once a day, once every three days or once a week. The compounds or compositions can be administered, for example, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

The method of the present invention may be practiced, for example, when relief of symptoms is specifically required or perhaps imminent. Alternatively, the method of the present invention may for example be effectively practiced as a continuous or prophylactic treatment.

The present invention also relates in part to a pharmaceutical composition, comprising a therapeutically effective amount of a compound of the present invention, or a pharmaceutically acceptable salt thereof, and a pharmaceutically acceptable carrier.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The present invention further relates to a method of agonizing glucose-dependent insulinotropic polypeptide in an individual comprising administering to the individual the compound of formula I, or a pharmaceutically acceptable salt thereof, in an amount effective in agonizing glucose-dependent insulinotropic polypeptide receptor.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose for intranasal administration is typically in the range of about 0.001 to about 0.1 mg/kg body weight. In humans, the preferred subcutaneous dose is from about 0.001 mg to about 100 mg; for example, from about 0.1 mg to about 15 mg.

In addition to the above, the present invention relates in part to the use of a compound according to formula I, or a pharmaceutically acceptable salt thereof, in the manufacture of a medicament. The medicament may be used, for example in the treatment of a metabolic disease or disorder. In an embodiment, the medicament may be used as an agonist of glucose-dependent insulinotropic polypeptide receptor.

EXAMPLES

The invention will be more fully understood by reference to the following examples. They should not, however, be construed as limiting the scope of the invention.

Abbreviations used herein are as follows.
$Et_2O$ diethyl ether
hr(s) hour(s)
TFA trifluoroacetic acid
TIS triisopropylsilane All solvents, isopropanol (iPrOH), methylene chloride ($CH_2Cl_2$), dimethylformamide (DMF) and N-methylpyrrolinone (NMP) were purchased from Fisher or Burdick & Jackson and were used without additional distillation.

Trifluoroacetic acid was purchased from Halocarbon or Fluka and used without further purification.

Diisopropylcarbodiimide (DIC) and diisopropylethylamine (DIPEA) were purchased from Fluka or Aldrich and used without further purification.

Hydroxybenzotriazole (HOBT), dimethylsulfide (DMS) and 1,2-ethanedithiol (EDT) were purchased from Sigma Chemical Co. and used without further purification.

Protected amino acids were generally of the L configuration and were obtained commercially from Bachem or Neosystem.

Purity of these reagents was confirmed by thin layer chromatography, NMR and melting point prior to use.

Benzhydrylamine resin (BHA) was a copolymer of styrene—1% divinylbenzene (100-200 or 200-400 mesh) obtained from Bachem or Advanced Chemtech. Total nitrogen content of these resins were generally between 0.3-1.2 meq/g.

High performance liquid chromatography (HPLC) was conducted on an automated Shimadzu HPLC with CLASS-VP-7.3 software system. Analytical HPLC was performed in reversed phase mode using Pursuit $C_{18}$ columns (4.5×50 mm).

Preparative HPLC separations were run on reversed phase Varian (Pursuit) or Waters (Xtera or Xbridge) $C_{18}$ columns (50×250 mm).

Example 1

The following is a protocol for a peptide synthesis at room temperature.
Protocol 1

| Step | Reagent | Time |
| --- | --- | --- |
| 1 | DMF | 2 × 30 sec |
| 2 | 20% piperidine/DMF | 5 min |
| 3 | 20% piperidine/DMF | 15 min |
| 4 | DMF | 2 × 30 sec |
| 5 | iPrOH | 2 × 30 sec |
| 6 | DMF | 3 × 30 sec |
| 7 | coupling | 60 min-18 hours |
| 8 | DMF | 2 × 30 sec |
| 9 | iPrOH | 1 × 30 sec |
| 10 | DMF | 1 × 30 sec |
| 11 | $CH_2Cl_2$ | 2 × 30 sec |

Solvents for all washings and couplings were measured to volumes of 10-20 ml/g resins. Coupling reactions throughout the synthesis were monitored by the Kaiser Ninhydrin test to determine extent of completion (Kaiser et at. Anal. Biochem. 34, 595-598 (1970)). Any incomplete coupling reactions were either recoupled with freshly prepared activated amino acid or capped by treating the peptide resin with acetic anhydride as described above. The fully assembled peptide-resins were dried in vacuum for several hours.

Example 2

The following example describes a protocol for microwave peptide synthesis.

A Liberty peptide synthesizer (CEM Corporation, Matthews, N.C.) was programmed for double coupling and capping by modification of the preloaded 0.25 mmol cycle using the software supplied by the manufacturer. The microwave editor was used to program microwave power methods for use during the Fmoc deprotection, amino acid coupling and capping with acetic anhydride. The default cycles for amino acid addition and final deprotection were selected in the cycle editor and were automatically loaded while creating the peptide.

The synthesis was carried out on a 0.25 mmol scale using Fmoc-Linker-BHA resin (450 mg, 0.25 mmol; available from AnaSpec, Inc., Fremont, Calif.). Deprotection was performed with a 20% piperidine in DMF solution. All coupling reactions were performed with 0.5M HBTU and 2M N-methyl morpholine (NMM) and were capped with 25% acetic anhydride in DMF after each amino acid coupling (protocol 2). Each deprotection, coupling and capping reaction was done using microwave at 75° C. for 360 seconds at 35 watts power and Nitrogen bubbling.

For each amino acid coupling, the following 0.25 mmol coupling cycle was used.
Protocol 2
Transfer resin to vessel
Add 20% Piperidine Deprotection (10 mL)
Microwave method for $1^{st}$ deprotection 30 sec at 75° C. max
Wash resin with DMF (10 mL)
Microwave method for $2^{nd}$ deprotection 180 sec at 75° C. max
Wash resin 3× with DMF (10 mL)
Add 0.2M Amino acid (5 mL)
Add 0.5M Activator (HBTU) (2 mL)
Add 2M Activator base (NMM) (1 mL)
Microwave method for Coupling 6 minutes at 75° C. max.
Wash resin 3× with DMF (10 mL)

The peptide was capped after the last amino acid coupling with 25% acetic anhydride in DMF (protocol 3)
Protocol 3
Wash resin 3× with DMF (10 mL)
Add 20% Piperidine Deprotection (10 mL)
Microwave method for $1^{st}$ deprotection 30 sec at 75° C. max
Wash resin with DMF (10 mL)
Microwave method for $2^{nd}$ deprotection 180 sec at 75° C. max
Wash resin 3× with DMF (10 mL)
Add capping (Acetic Anhydride 10 mL)
Microwave Method (capping) 180 sec at 75° C. max
Wash resin 3× with DMF (10 mL)

Example 3

This example describes the preparation of $PEG_m(30,000)$—SSA. Similar procedures were followed to produce $PEG_m(12,000)$—SSA and $PEG_m(20,000)$—SSA.

Synthesis of $PEG_m(30,000)$-Mesylate

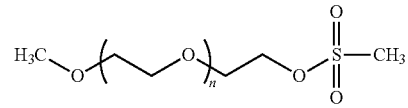

Where n~682

A round-bottom flask equipped with a magnetic stirrer, dean-stark trap, reflux condenser and argon inlet bubbler was charged with 100 g (3.34 mmol) of $PEG_m(30,000)$—OH and 500 mL of toluene. The PEG solution in toluene was azeotropically dried by distillation and then cooled to room temperature. Two hundred mL of anhydrous dichloromethane was added and the solution was cooled to 0-5° C. Triethylamine (0.67 mL, 4.84 mmol) and methanesulfonyl chloride (0.33 mL, 4.34 mmol) were added and the mixture was stirred for 2 hours at ca. 4° C. and then at room temperature overnight under argon.

Methylene chloride was removed under reduced pressure using a rotary evaporator. Residual salt was filtered out and the product was precipitated with cold isopropyl alcohol and diethyl ether (30:70, v/v). The product was collected and dried under vacuum at room temperature. The yield was ~90%.

Synthesis of $PEG_m(30,000)$-Amine

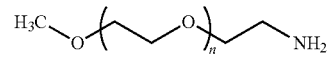

Where n~682

A round-bottom flask equipped with a magnetic stirrer and argon inlet bubbler was charged with 90 g (3.00 mmol) of $PEG_m(30,000)$-mesylate and 1600 mL of ammonium hydroxide aqueous solution (30%, v/v). Ammonium chloride (160 g) was added and the solution was stirred for 48 hours at room temperature. Sodium chloride 160 g (10 wt %) was added and the PEG amine was extracted with dichloromethane. The combined organic extracts were dried over anhydrous sodium sulfate. The sodium sulfate was filtered off and the remaining methylene chloride was removed on a rotary evaporator. The product was precipitated with cold diethyl ether. The product was collected and dried overnight under vacuum at room temperature. The yield was ~94%.

Synthesis of $PEG_m$(30,000)-Succinamide Acid (SAA)

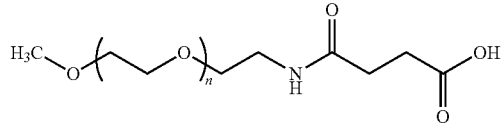

Where n~682

A round-bottom flask equipped with a magnetic stirrer and argon inlet bubbler was charged with 60 g (2.00 mmol) of $PEG_m$(30,000)-amine and 500 mL of anhydrous acetonitrile. The solution was cooled down to ca. 4° C., then 2 g (20.0 mmol) of succinic anhydride in 50 mL of anhydrous acetonitrile was added slowly through an addition funnel. The reaction mixture was stirred at room temperature overnight under argon.

Upon completion, the solvent was removed using a rotary evaporator and then the product was dissolved in 400 mL of water. The pH of the solution was adjusted to 7.0 with 1 M NaOH solution and stirred for 1 h. Sodium chloride (40 g, 10 wt. %) was added and the pH was adjusted to ~4.2 with 6 N HCl solution. The product was extracted 3 times with dichloromethane. The combined organic extracts were dried over anhydrous sodium sulfate. Sodium sulfate was removed by filtration and the filtrate was concentrated using a rotary evaporator. The product was precipitated with cold diethyl ether. The product was collected and dried overnight under vacuum. The yield was ~93%.

Synthesis of $PEG_m$(30,000)-Succinimidyl Succinamide (SSA)

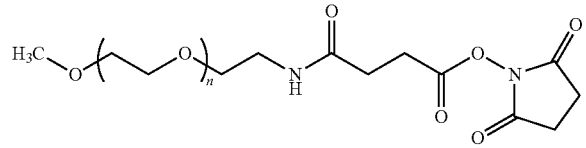

Where n~682

A round-bottom flask equipped with a magnetic stirrer and argon inlet bubbler was charged with 56 g (1.87 mmol) of $PEG_m$(30,000)-succinamide acid and 500 mL of anhydrous dichloromethane. N-hydroxysuccinimide (0.24 g, 2.05 mmol) and 1,3-dicyclohexylcarbodiimide (0.46 g, 2.24 mmol) were added slowly. The reaction mixture was stirred at room temperature overnight under argon.

Upon completion, the solvent was removed using a rotary evaporator. The product was then dissolved in anhydrous toluene. Residual salt was removed by filtration and the product was precipitated in cold anhydrous isopropyl alcohol and diethyl ether (30:70, v/v). The product was collected and dried overnight under vacuum at room temperature. The yield was 80%.

Example 4

Synthesis of H-Tyr-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-Gly-Lys-Lys-Asn-Asp-Trp-Lys-His-Asn-Ile-Thr-Gln-OH (SEQ ID NO: 1) 1:6 TFA The above peptide was synthesized using Fmoc chemistry on a CEM microwave peptide synthesizer. The synthesizer was programmed for double coupling using the modules described in protocol 2. The synthesis was carried out on a 0.25 0 mmol scale using the Fmoc Gln(Trt) Wang resin (Sub: 6 meq/g; used 400 mg). At the end of the synthesis, the resin was transferred to a reaction vessel on a shaker for cleavage. The peptide was cleaved from the resin using 17 mL of 97% TFA (3% water) and 1 mL of TIS and propane thiol (1:2) at room temperature for 1.5 hrs. The deprotection solution was added to 100 mL cold $Et_2O$, and washed with 1 mL TFA and 30 mL cold $Et_2O$ to precipitate the peptide. The peptide was centrifuged in 2×50 mL polypropylene tubes. The precipitates from the individual tubes were combined in a single tube and washed 3 times with cold $Et_2O$ and dried in a desiccator under house vacuum.

The crude peptide was purified by preparative HPLC (Shimadzu) on a Xtera C18-Column (250×50 mm, 10 μm particle size) and eluted with a linear gradient of 10-99% B (buffer A: 0.1% TFA/$H_2O$; buffer B: 0.1% TFA/$CH_3CN$) in 90 min., flow rate 60 mL/min, and detection 220/280 nm. The fractions were collected and checked by analytical HPLC. All analytical runs were performed on a Shimadzu HPLC using $C_{18}$ reverse phase Waters Xtera/pursuit 4.6×50 columns using a gradient of 10-99% using A: 0.1% Water/TFA and B: 0.1% Acetonitrile/TFA. Fractions containing pure product were combined and lyophilized to yield 138 mg (6.1%) of a white amorphous powder. (ES)+–LCMS m/e calculated ("calcd") for $C_{226}H_{338}N_{60}O_{66}S$ 4983.64. found 4983.62.

Example 5

Synthesis of Ac-Tyr-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-$NH_2$ (SEQ ID NO: 2) 1:2 TFA The above peptide was synthesized using Fmoc chemistry on CEM microwave peptide synthesizer. The synthesizer was programmed for double coupling using the modules described in protocols 2 and 3. The synthesis was carried out on a 0.25 mmol scale using the Fmoc Rink Amide MBHA resin (Sub: 0.45 meq/g; used 450 mg). At the end of the synthesis, the resin was transferred to a reaction vessel on a shaker for cleavage. The peptide was cleaved using 17 mL of 97% TFA (3% water) and 1 mL of TIS and propane thiol (1:2) at room temperature for 1.5 hrs. The deprotection solution was added to 100 mL cold $Et_2O$, and washed with 1 mL TFA and 30 mL cold $Et_2O$ to precipitate the peptide. The peptide was centrifuged in 2×50 mL polypropylene tubes. The precipitates from the individual tubes were combined in a single tube and washed 3 times with cold $Et_2O$ and dried in a desiccator under house vacuum.

The crude peptide was purified by preparative HPLC (Shimadzu) on a Xtera C18-Column (250×50 mm, 10 μm particle size) and eluted with a linear gradient of 10-99% B (buffer A: 0.1% TFA/$H_2O$; buffer B: 0.1% TFA/$CH_3CN$) in 90 min., flow rate 60 mL/min, and detection 220/280 nm. The fractions were collected and checked by analytical HPLC. All analytical runs were performed on Shimadzu HPLC using C18 reverse phase Waters Xtera/pursuit 4.6×50 columns using gradient from 10-99% using A: 0.1% Water/TFA and B:0.1% Acetonitrile/TFA. Fractions containing pure product were combined and lyophilized to yield 180 mg (18.9%) of a white amorphous powder. (ES)+-LCMS m/e calculated ("calcd") for $C_{164}H_{242}N_{400}O_{48}S$ 3574.06. found 3574.04.

Example 6

Synthesis of Ac-(D)Tyr-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-$NH_2$ (SEQ ID NO: 3) 1:2 TFA Fmoc Rink Amide MBHA resin (450 mg, 0.25 mmol) was subjected to solid phase synthesis and purification by following the procedure in example 5 to yield 108 mg (11.4%) of white amorphous powder. (ES)+-LCMS m/e calculated ("calcd") for $C_{164}H_{242}N_{40}O_{48}S$ 3574.06. found 3574.04

Example 7

Synthesis of $DesNH_2$-Tyr-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-$NH_2$ (SEQ ID NO: 4) 1:2 TFA Fmoc Rink Amide MBHA resin (450 mg, 0.25 mmol) was subjected to solid phase synthesis and purification by following the procedure in example 5 to yield 70 mg (7%) of white amorphous powder. (ES)+-LCMS m/e calculated ("calcd") $C_{162}H_{239}N_{39}O_{47}S$ 3517.01. found 3516.91.

Example 8

Synthesis of Ac-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-$NH_2$ (SEQ ID NO: 5) 1:2 TFA Fmoc Rink Amide MBHA resin (450 mg, 0.25 mmol) was subjected to solid phase synthesis and purification by following the procedure in example 5 to yield 80 mg (8.3%) of white amorphous powder. (ES)+-LCMS m/e calculated ("calcd") $C_{164}H_{242}N_{40}O_{47}S$ 3558.06. found 3558.11.

Example 9

Synthesis of $DesNH_2$-Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-$NH_2$ (SEQ ID NO: 6) 1:2 TFA Fmoc Rink Amide MBHA resin (450 mg, 0.25 mmol) was subjected to solid phase synthesis and purification by following the procedure in example 5 to yield 120 mg (12.7%) of white amorphous powder. (ES)+-LCMS m/e calculated ("calcd") $C_{162}H_{239}N_{39}O_{46}S$ 3501.01. found 3500.98.

Example 10

Synthesis of Ac-(D)Trp-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-$NH_2$ (SEQ ID NO: 7) 1:2 TFA Fmoc Rink Amide MBHA resin (450 mg, 0.25 mmol) was subjected to solid phase synthesis and purification by following the procedure in example 5 to yield 62 mg (6.4%) of white amorphous powder. (ES)+-LCMS m/e calculated ("calcd") $C_{166}H_{243}N_{41}O_{47}S$ 3597.10. found 3596.99.

Example 11

Synthesis of Ac-(D)-3-Pya-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-$NH_2$ (SEQ ID NO: 8) 1:2 TFA Fmoc Rink Amide MBHA resin (450 mg, 0.25 mmol) was subjected to solid phase synthesis and purification by following the procedure in example 5 to yield 40 mg (4%) of white amorphous powder. (ES)+-LCMS m/e calculated ("calcd") for $C_{163}H_{241}N_{41}O_{47}S$ 3559.05. found 3559.01.

Example 12

Synthesis of Ac-2-Cl-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-$NH_2$ (SEQ ID NO: 9) 1:2 TFA Fmoc Rink Amide MBHA resin (450 mg, 0.25 mmol) was subjected to solid phase synthesis and purification by following the procedure in example 5 to yield 94 mg (9.7%) of white amorphous powder. (ES)+-LCMS m/e calculated ("calcd") for $C_{164}H_{241}ClN_{40}O_{47}S$ 3592.51. found 3592.49.

Example 13

Synthesis of Ac-3-Cl-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-$NH_2$ (SEQ ID NO: 10) 1:2 TFA Fmoc Rink Amide MBHA resin (450 mg, 0.25 mmol) was subjected to solid phase synthesis and purification by following the procedure in example 5 to yield 70 mg (7.2%) of white amorphous powder. (ES)+-LCMS m/e calculated ("calcd") for $C_{164}H_{241}Cl N_{40}O_{47}S$ 3592.51. found 3592.48.

Example 14

Synthesis of Ac-4-Cl-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-$NH_2$ (SEQ ID NO: 11) 1:2 TFA Fmoc Rink Amide MBHA resin (450 mg, 0.25 mmol) was subjected to solid phase synthesis and purification by following the procedure in example 5 to yield 96 mg (10%) of white amorphous powder. (ES)+-LCMS m/e calculated ("calcd") for $C_{164}H_{241}ClN_{40}O_{47}S$ 3592.51. found 3592.50.

Example 15

Synthesis of Ac-2-F-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 12) 1:2 TFA Fmoc Rink Amide MBHA resin (450 mg, 0.25 mmol) was subjected to solid phase synthesis and purification by following the procedure in example 5 to yield 92 mg (9.5%) of white amorphous powder. (ES)+-LCMS m/e calculated ("calcd") for $C_{164}H_{241}FN_{40}O_{47}S$ 3576.05. found 3576.04.

Example 16

Synthesis of Ac-3-F-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 13) 1:2 TFA Fmoc Rink Amide MBHA resin (450 mg, 0.25 mmol) was subjected to solid phase synthesis and purification by following the procedure in example 5 to yield 100 mg (10.4%) of white amorphous powder. (ES)+-LCMS m/e calculated ("calcd") for $C_{164}H_{241}FN_{40}O_{47}S$ 3576.05. found 3576.04.

Example 17

Synthesis of Ac-3,5-DiF-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 14) 1:2 TFA Fmoc Rink Amide MBHA resin (450 mg, 0.25 mmol) was subjected to solid phase synthesis and purification by following the procedure in example 5 to yield 64 mg (6.6%) of white amorphous powder. (ES)+-LCMS m/e calculated ("calcd") for $C_{164}H_{240}F_2N_{40}O_{47}S$ 3594.04. found 3593.99.

Example 18

Synthesis of Ac-3,4,5,F3-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 15) 1:2 TFA Fmoc Rink Amide MBHA resin (450 mg, 0.25 mmol) was subjected to solid phase synthesis and purification by following the procedure in example 5 to yield 30 mg (3%) of white amorphous powder. (ES)+-LCMS m/e calculated ("calcd") for $C_{164}H_{239}F_3N_{40}O_{47}S$ 3612.03. found 3612.01.

Example 19

Synthesis of Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys-NH$_2$ (SEQ ID NO: 16) 1:1 TFA Fmoc Rink Amide MBHA resin (450 mg, 0.25 mmol) was subjected to solid phase synthesis and purification by following the procedure in example 5 to yield 80 mg (9%) of white amorphous powder. (ES)+-LCMS m/e calculated ("calcd") for $C_{161}H_{235}N_{39}O_{48}S$ 3516.96. found 3516.94.

Analytical Method for Examples 20 to 22

The test and control articles were analyzed using the following reversed-phase HPLC/UV procedure:
Instrument Waters Acquity System with Photodiode Array Detector
Injection Volume 2 μL
Injector Temperature Ambient
Detector Wavelength 280 nm
Column Acquity BEH-C8, 1.8 micron, 50 mm×2.1 mm i.d.
Column Temperature 25° C.
Flow Rate 0.25 mL/minute (5000 psi)
Mobile Phase A Water containing 0.05% TFA
Mobile Phase B Acetonitrile containing 0.05% TFA
Run Time Approximately 10 minutes
Sample Preparation Approximately 0.2-0.5 mg/ml
Diluent Deionized water
Mobile Phase Gradient Condition (RP-HPLC):

| Time, minutes | % Mobile Phase A | % Mobile Phase B | Condition |
| --- | --- | --- | --- |
| 0 | 75 | 25 | Linear ramp |
| 5 | 15 | 85 | |
| 6 | 15 | 85 | Equilibrium |
| 7 | 75 | 25 | Equilibrium |
| 10 | 75 | 25 | Equilibrium |

Example 20

Synthesis of Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(12,000))-NH$_2$ A PEG$_m$(12,000) moiety was conjugated to the compound from Example 19.

10 mg of the peptide from Example 19 was weighed out and dissolved in 50 mM borate, pH 8.5 buffer. 130 mg PEG$_m$ (12,000)-succinimidyl succinamide, as prepared following the procedure of Example 3, was weighed to achieve a 4:1 PEG:peptide molar ratio and added to the dissolved peptide. The reaction mixture was agitated at room temperature overnight before it was diluted 10-fold in 20 mM Tris, pH 8.0 buffer and purified by anion exchange chromatography on Q-Sepharose® FF (GE Healthcare). FIG. 1 is an RP-HPLC chromatogram of the reaction mixture. The reaction yielded 38.1% PEGylated peptide.

Mono-PEGylated peptide was eluted using a step NaCl gradient. The desired mono-PEGylated peptide eluted with 200 mM NaCl. The eluate was acidified with 1M NaOAc and concentrated in an Amicon ultrafiltration cell using a 3 kDa MW cutoff membrane. It was then diafiltered 10-fold once with 20 mM NaOAc, pH 4.5.

Figure 2:
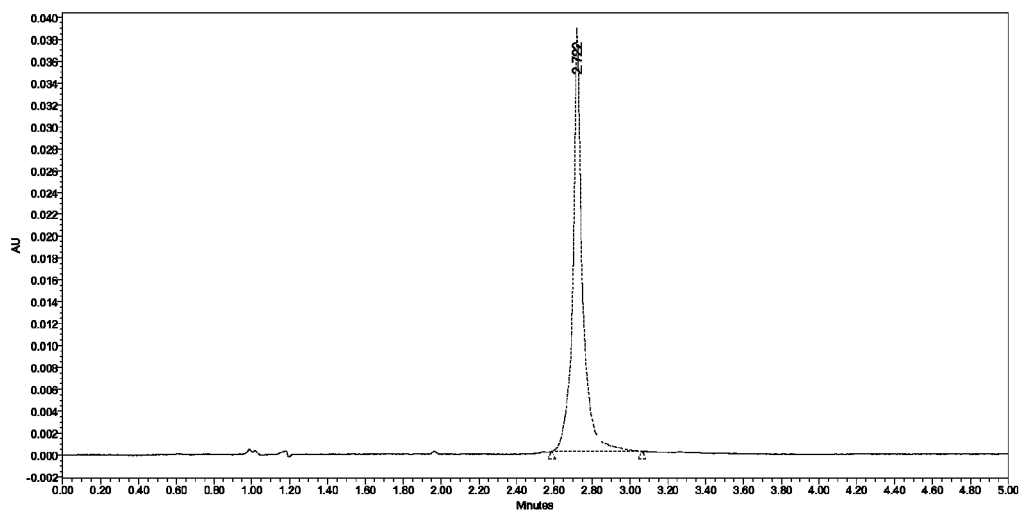
FIG. 2 shows an RP-HPLC chromatogram of the purified compound of Example 20.
Figure 3:
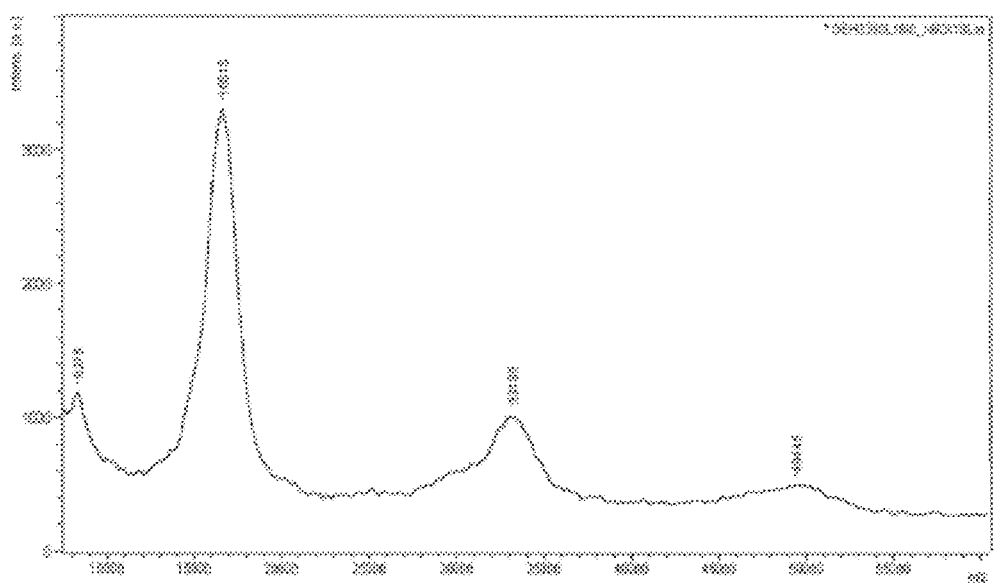
FIG. 3 shows a MALDI-TOF spectrum of the compound of Example 20.

The concentrated PEGylated peptide was then submitted for analysis, assayed and stored at 4° C. FIG. 2 is an RP-HPLC chromatogram of purified PEG$_m$(12,000)-peptide (RT=2.72 min). Purity of PEGylated peptide was determined to be >98%. FIG. 3 is a graph representing a MALDI-TOF spectrum of the PEG$_m$(12,000)-peptide, which was performed to confirm the molecular weight.

Example 21

Preparation of Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(20,000))-NH$_2$ A PEG$_m$(20,000) moiety was conjugated to the compound from Example 19.

Figure 4:
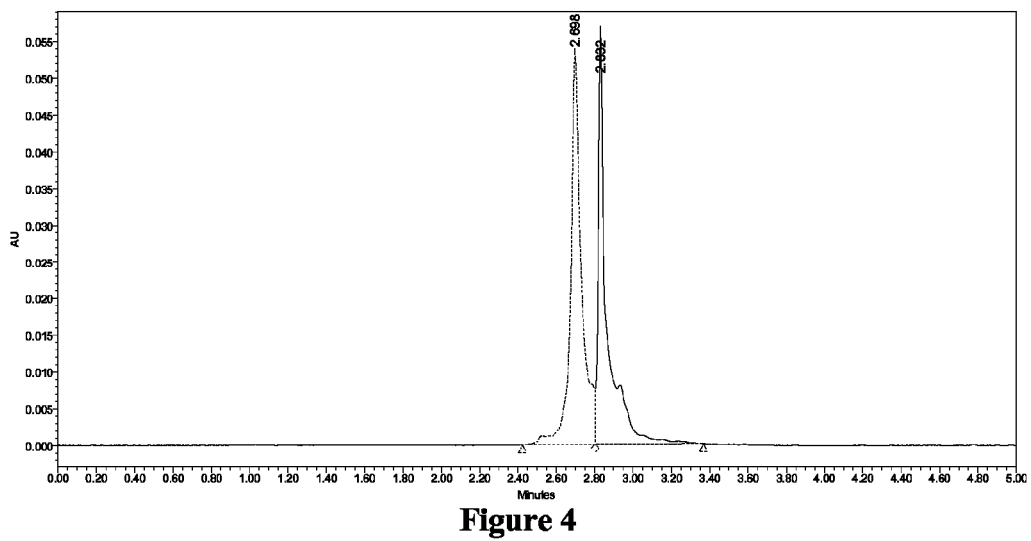
FIG. 4 shows an RP-HPLC chromatogram of a reaction mixture containing the compound of Example 21.

10 mg of peptide from Example 19 was weighed out and dissolved in 50 mM Borate, pH 8.5 buffer. 225 mg PEG$_m$(20,000)-succinimidyl succinamide, as prepared following the procedure of Example 3, was weighed to achieve a 4:1 PEG:peptide molar ratio and added to the dissolved peptide. The reaction mixture was agitated at room temperature overnight before it was diluted 10-fold in 20 mM Tris, pH 8.0 buffer and purified by anion exchange chromatography on Q-Sepharose® FF (GE Healthcare). FIG. 4 is an RP-HPLC chromatogram of the reaction mixture. The reaction yielded 54.9% PEGylated peptide.

Mono-PEGylated peptide was eluted using a step NaCl gradient. The desired mono-PEGylated peptide is eluted with 200 mM NaCl. The eluate was acidified with 1M NaOAc and concentrated in an Amicon ultrafiltration cell using a 3 kDa MW cutoff membrane. It was then diafiltered 10-fold once with 20 mM NaOAc, pH 4.5.

Figure 5:
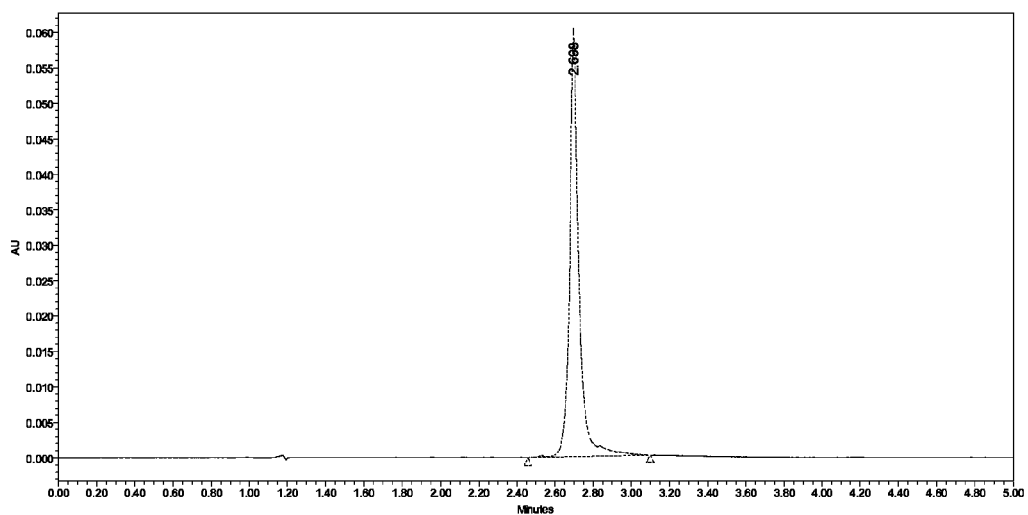
FIG. 5 shows an RP-HPLC chromatogram of the purified compound of Example 21.
Figure 6:
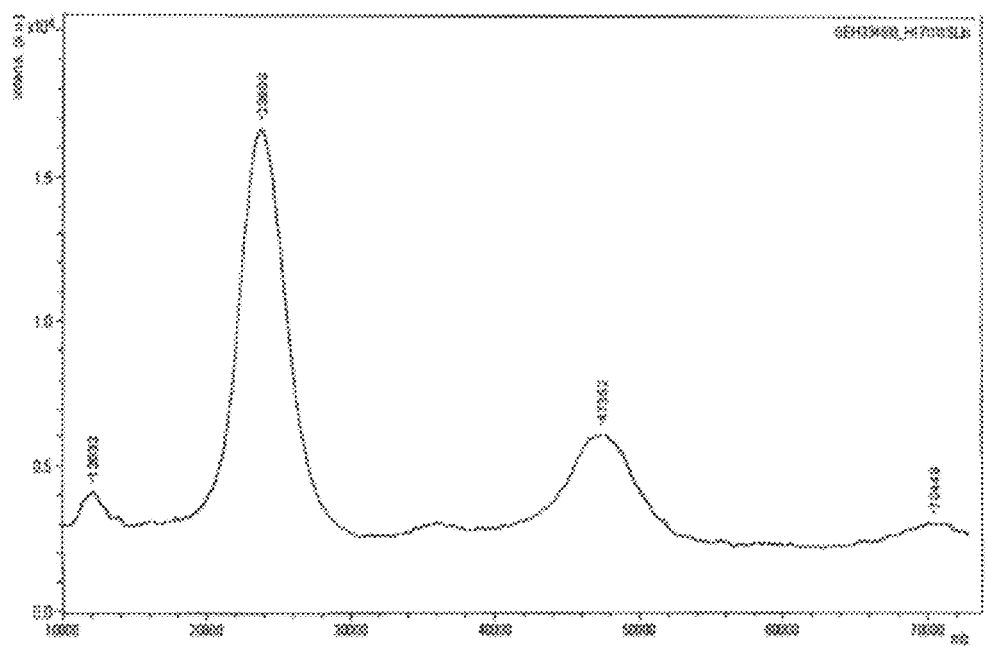
FIG. 6 shows a MALDI-TOF spectrum of the compound of Example 21.

The concentrated PEGylated peptide was submitted for analysis, assayed and stored at 4° C. FIG. 5 is an RP-HPLC chromatogram of purified PEG$_m$(20,000)-peptide (RT=2.70 min). Purity of the PEGylated peptide was determined to be >98%. FIG. 6 is a graph representing a MALDI-TOF spectrum of the PEG$_m$(20,000)-peptide, which was performed to confirm the molecular weight.

Example 22

Preparation of Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys (epsilon-SSA-PEG$_m$(30,000))-NH$_2$ A PEG$_m$(30,000) moiety was conjugated to the compound from Example 19.

Figure 7:
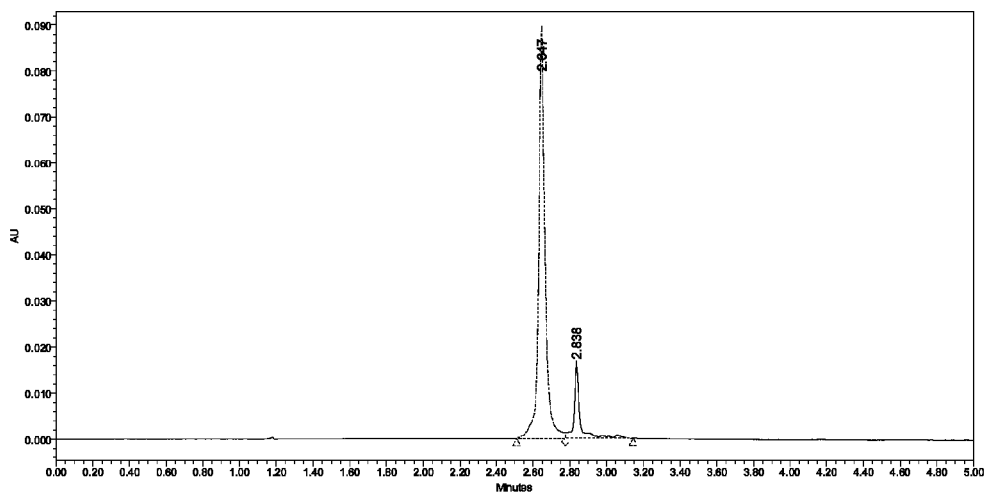
FIG. 7 shows an RP-HPLC chromatogram of a reaction mixture containing the compound of Example 22.

50 mg of peptide from Example 19 was weighed out and dissolved in 50 mM Borate, pH 8.5 buffer. 1625 mg PEG$_m$(30,000)-succinimidyl succinamide, as prepared following the procedure of Example 3, was weighed to achieve a 4:1 PEG:peptide molar ratio and added to the dissolved peptide. The reaction mixture was agitated at room temperature overnight before it was diluted 10-fold in 20 mM Tris, pH 8.0 buffer and purified by anion exchange chromatography on Q-Sepharose® FF (GE Healthcare). FIG. 7 is an RP-HPLC chromatogram of the reaction mixture. The reaction yielded 85.0% PEGylated peptide.

Mono-PEGylated peptide was eluted using a step NaCl gradient. Typically, the desired mono-PEGylated peptide eluted with 200 mM NaCl. The eluate was acidified with 1M NaOAc and concentrated in an Amicon ultrafiltration cell using a 3 kDa MW cutoff membrane. It was then diafiltered 10-fold once with 20 mM NaOAc, pH 4.5.

Figure 8:
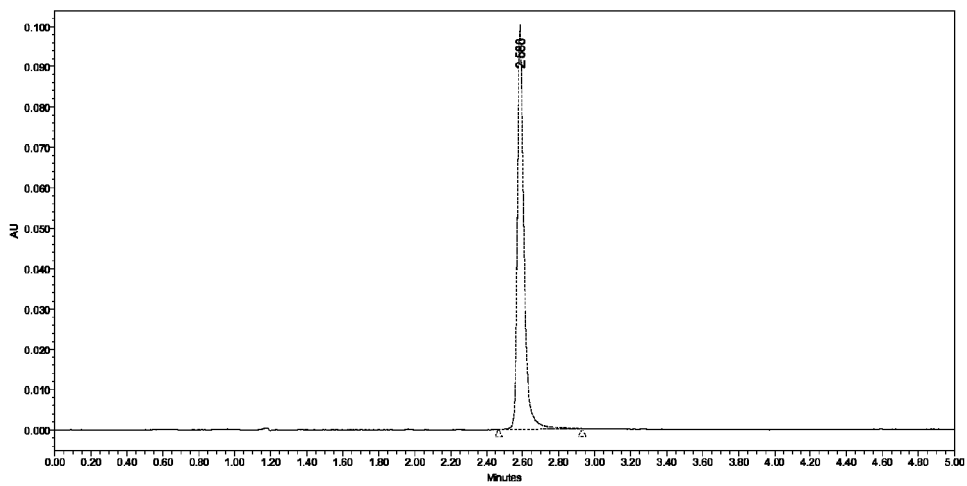
FIG. 8 shows an RP-HPLC chromatogram of the purified compound of Example 22.
Figure 9:
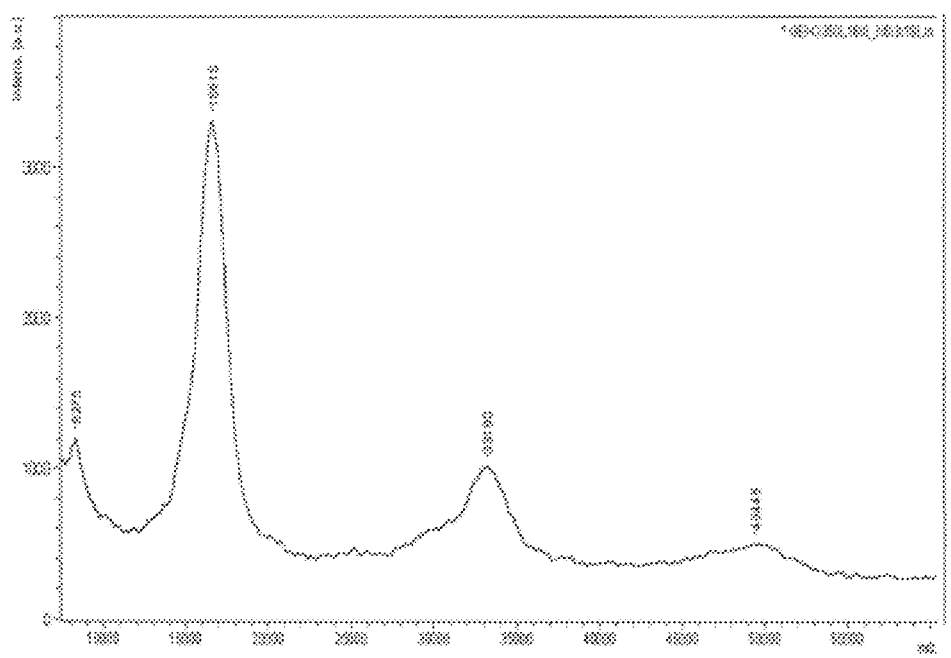
FIG. 9 shows a MALDI-TOF spectrum of the compound of Example 22.

The concentrated PEGylated peptide was submitted for analysis, assayed and stored at 4 C. FIG. 8 is an RP-HPLC chromatogram of purified PEG$_m$(30,000)-peptide (RT=2.59 min). Purity of the PEGylated peptide was determined to be >98%. FIG. 9 is a graph representing a MALDI-TOF spectrum of the PEG$_m$(30,000)-peptide, which was performed to confirm the molecular weight.

Example 23

The following study was conducted to assess the stability of the compound of Example 19 in Hannover Wistar rat and human plasma after 4 and 24 hours.

2.08 mg of the compound of Example 19 was weighed out and placed in a 4 mL amber vial. To this was added 1.0 mL DMSO. The vial was carefully vortexed to produce a 573 µM stock solution of the compound.

Hannover Wistar rat plasma and human plasma (anti-coagulant sodium EDTA) were pre-warmed to 37° C. for 30 minutes in a water bath. Rat plasma pH was 7.45 and human plasma pH was 7.47. 1.5 mL microcentrifuge vials were used.

8.70 µL of 573 µM stock solution of the compound of Example 19 was added to 491.34 µL of the rat plasma and placed into one vial. 8.74 µL of 573 µM stock solution of the compound of Example 19 was added to 491.34 µL of the human plasma and placed into another vial. The two vials were gently vortexed ensuring proper mixing.

Six new vials were labeled as follows: rat $T_0$, rat $T_4$, rat $T_{24}$, human $T_0$, human $T_4$, human $T_{24}$. To each of these vials, 504 of treated plasma was added. The $T_4$ and $T_{24}$ vials were capped and placed in a 37° C. incubator for 4 and 24 hours, respectively.

To each of the two $T_0$ vials, 504 of Sorensen buffer and 200 µL 1.0% acetic acid in acetonitrile were added. The $T_0$ vials were then capped, vortexed and centrifuged at 10000×g for 10 minutes. Upon completion of centrifugation, 100 µL of the supernatant of each vial was added to a separate well in a 96-well injection block. 200 µL of 0.1% acetic acid in Milli-Q® water (Millipore) was then added to each well.

The above procedure as written with respect to the $T_0$ vials was repeated for the two $T_4$ vials at the 4 hour timepoint and the $T_{24}$ vials at the 24 hour timepoint. With each timepoint a fresh $T_0$ sample was prepared, as described above, to ensure there was no sample degradation.

All samples were analyzed by LC/MS/MS. The resulting chromatographs were processed to obtain peaks areas for each sample. The percent of compound remaining at each timepoint as compared with the amount present in the comparison $T_0$ sample was calculated.

|  | Rat | | Human | |
| --- | --- | --- | --- | --- |
| Conc. (10 uM) | % Remaining 4 hr | % Remaining 24 hr | % Remaining 4 hr | % Remaining 24 hr |
|  | 124.7 | 72.7 | 93.6 | 75.9 |

The data indicate that the compound was stable in rat plasma at 4 hours but slightly below the acceptance range (75-125%) at the 24 hour timepoint. The peptide was stable for both the 4 hour and the 24 hour timepoints in human plasma.

Example 24

CHO—K1 cells expressing human GIPR were obtained from DiscoverX Corporation (Fremont, Calif.). The cells were cultured in Ham's F-12 nutrient media supplemented with 10% foetal bovine serum, 800 µg/ml geneticin, 300 µg/ml hydromycin, 2 mM L-glutamine, and Penicillin-streptomycin (100 units, 100 μg) at 37° C. in a 5% CO incubator. The cells were harvested at 90% confluence.

The cells were suspended in Ham's F-12 nutrient media to a concentration of 200,000 cells/ml. The cells were then plated in a 384 well plate at with 0.025 rat of the suspension added per well. The cells were incubated overnight at 37° C. in a 5% $CO_2$ incubator.

The activity of the compounds was determined by stimulating the CHO—K1 cells with the test compound, and measuring the levels of cAMP produced. The activity of the compounds was compared to the activity of native GIP, as GIP stimulates cAMP production. 6 μl of the test compound in stimulation buffer (990 ml Hank's Balanced Salt solution (HBSS) (1×) (Invitrogen Corp #14025-092), 10 ml Hepes buffer solution (1 mol·L) (Invitrogen Corp 15630-080), 1 g BSA (final 0.1%), and 1 ml IBMX 250 mM stock prepared fresh in DMSO (Sigma-Aldrich 15879)) were added to cells, followed by 6 μl of Alexa Fluor® 647-anti cAMP antibody (Perkin Elmer) in stimulation buffer. In addition, 6 μl of native GIP (compound of Example 4) in stimulation buffer was added to the cells in one well as a control. The well plate was centrifuged for 3 min at 300 rpm, and incubated at room temperature for 45 minutes. 12 μl of detection mixture (biotin cAMP and EUW8044 labeled streptavidin (Eu-SA) in cAMP Detection Buffer (Perkin Elmer)) was added and incubated for 60 min at room temperature.

The levels of cAMP produced were measured according to the detailed protocol outlined in the Perkin Elmer LANCE cAMP Assay Perkin Elmer Lance cAMP Kit manual. The activity of the compounds was compared to the activity of native GIP.

The plates are read on a TRF detection instrument, EnVision® (Perkin Elmer) (excitation at 340 nM and emission at 665 nM). The values of the cAMP signal are obtained from the standard cAMP curve and used to determine the amount of maximal stimulation, and EC50 for stimulating the cAMP signal.

| EC50 (nMol) | |
|---|---|
| Example | % activation of cAMP |
| 4 | 0.004 (100%) |
| 5 | 0.008 (100%) |
| 6 | 0.0007 (102%) |
| 7 | 0.095 (103%) |
| 8 | 0.685 (102%) |
| 9 | 0.797 (101%) |
| 10 | 0.1 (102%) |
| 11 | 0.080 (102%) |
| 12 | 0.121 (104%) |
| 13 | 0.072 (106%) |
| 14 | 0.025 (106%) |
| 15 | 0.0075 (99.8%) |
| 16 | 0.058 (98%) |
| 17 | 0.0030 (99.6%) |
| 18 | 0.104 (100%) |
| 19 | 0.0005 (100%) |
| 20 | 0.0022 (100%) |
| 21 | 0.0049 (102%) |
| 22 | 0.0017 (101%) |

The invention claimed is:

1. A compound having the formula (I):

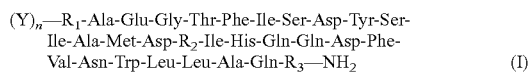

(Y)$_n$—R$_1$-Ala-Glu-Gly-Thr-Phe-Ile-Ser-Asp-Tyr-Ser-
Ile-Ala-Met-Asp-R$_2$-Ile-His-Gln-Gln-Asp-Phe-
Val-Asn-Trp-Leu-Leu-Ala-Gln-R$_3$—NH$_2$    (I)

wherein:
R$_1$ is selected from the group consisting of: (D)Tyr; DesNH$_2$-Tyr; (D)Phe; DesNH$_2$-Phe; (D)Trp; (D)3Pya; 2-Cl(D)Phe; 3-Cl(D)Phe; 4-Cl(D)Phe; 2-F(D)Phe; 3-F (D)Phe; 3,5 DiF(D)Phe; and 3,4,5TriF(D)Phe;
R$_2$ is Lys or Ala;
R$_3$ is Lys or PEGylated Lys;
Y is acyl;
n is 1 when R$_1$ is (D)Tyr; (D)Phe; (D)Trp; (D)3Pya; 2-Cl-(D)Phe; 3-Cl-(D)Phe; 4-Cl-(D)Phe; 2-F-(D)Phe; 3-F-(D)Phe; 3,5-DiF(D)Phe; or 3,4,5-TriF(D)Phe; and
n is 0 when R$_1$ is DesNH$_2$-Tyr; (D)Phe or DesNH$_2$-Phe;
or a pharmaceutically-acceptable salt thereof.

2. A compound of claim 1 wherein R$_1$ is (D)Tyr or DesNH$_2$-Tyr.

3. A compound of claim 1 wherein R$_1$ is (D)Tyr.

4. A compound of claim 1 wherein R$_1$ is selected from the group consisting of: (D)Phe; DesNH$_2$-Phe; 2-Cl-(D)Phe; 3-Cl-(D)Phe; 4-Cl-(D)Phe; 2-F-(D)Phe; 3-F-(D)Phe; 3,5-DiF-(D)Phe; and 3,4,5-TriF-(D)Phe.

5. A compound of claim 1 wherein R$_1$ is (D)Trp.

6. A compound of claim 1 wherein R$_1$ is (D)3Pya.

7. A compound of claim 1 wherein R$_2$ is Lys.

8. A compound of claim 1 wherein R$_2$ is Ala.

9. A compound of claim 1 wherein R$_3$ is Lys.

10. A compound of claim 1 wherein R$_3$ is PEGylated Lys.

11. A compound of claim 1 wherein R$_3$ is Lys-PEG.

12. A compound of claim 1 wherein R$_3$ is Lys-PEG$_m$.

13. A compound of claim 1 wherein R$_3$ is PEGylated Lys wherein the PEG moiety has a molecular weight of from about 5,000 to about 40,000 Daltons.

14. A compound of claim 1 wherein R$_3$ is PEGylated Lys wherein the PEG moiety has a molecular weight of from about 10,000 to about 30,000 Daltons.

15. A compound of claim 1 wherein R$_3$ is PEGylated Lys wherein the PEG moiety has a molecular weight of from about 15,000 to about 25,000 Daltons.

16. A compound of claim 1 wherein R$_3$ is PEGylated Lys wherein the PEG moiety has a molecular weight of about 20,000 Daltons.

17. A compound of claim 1 wherein R$_3$ is Lys-PEG$_m$ wherein the PEG$_m$ has a molecular weight of from about 5,000 to about 40,000 Daltons.

18. A compound of claim 1 wherein R$_3$ is Lys-PEG$_m$ wherein the PEG$_m$ has a molecular weight of from about 10,000 to about 30,000 Daltons.

19. A compound of claim 1 wherein R$_3$ is Lys-PEG$_m$ wherein the PEG$_m$ has a molecular weight of from about 15,000 to about 25,000 Daltons.

20. A compound of claim 1 wherein R$_3$ is Lys-PEG$_m$ wherein the PEG$_m$ has a molecular weight of about 20,000 Daltons.

21. A compound of claim 1 wherein R$_3$ is Lys (epsilon-SSA-PEG$_m$).

22. A compound of claim 1 wherein R$_3$ is selected from the group consisting of: Lys(epsilon-SSA-PEG$_m$(12,000)), Lys (epsilon-SSA-PEG$_m$(20,000)), and Lys(epsilon-SSA-PEG$_m$ (30,000)).

37

23. A compound of claim 1 wherein $R_3$ is Lys(epsilon-SSA-PEG$_m$(20,000)).

24. A compound of claim 1 wherein $R_1$ is (D)Tyr or DesNH$_2$-Tyr and $R_2$ is Ala.

25. A compound of claim 1 wherein $R_1$ is (D)Tyr or DesNH$_2$-Tyr, $R_2$ is Ala, and $R_3$ is PEGylated Lys.

26. A compound of claim 1 wherein $R_1$ is (D)Tyr or DesNH$_2$-Tyr, $R_2$ is Ala, and $R_3$ is PEGylated Lys wherein the PEG moiety a molecular weight of from about 5,000 to about 40,000 Daltons.

27. A compound of claim 1 wherein $R_1$ is (D)Tyr or DesNH$_2$-Tyr, $R_2$ is Ala, and $R_3$ is PEGylated Lys wherein the PEG moiety has a molecular weight of from about 10,000 to about 30,000 Daltons.

28. A compound of claim 1 wherein $R_1$ is (D)Tyr or DesNH$_2$-Tyr, $R_2$ is Ala, and $R_3$ is PEGylated Lys wherein the PEG moiety has a molecular weight of from about 15,000 to about 25,000 Daltons.

29. A compound of claim 1 wherein $R_1$ is (D)Tyr or DesNH$_2$-Tyr, $R_2$ is Ala, and $R_3$ is PEGylated Lys wherein the PEG moiety has a molecular weight of about 20,000 Daltons.

30. A compound of claim 1 wherein $R_1$ is (D)Tyr or DesNH$_2$-Tyr, $R_2$ is Ala, and $R_3$ is Lys-PEG$_m$ wherein the PEG$_m$ has a molecular weight of from about 5,000 to about 40,000 Daltons.

31. A compound of claim 1 wherein $R_1$ is (D)Tyr or DesNH$_2$-Tyr, $R_2$ is Ala, and $R_3$ is Lys-PEG$_m$ wherein the PEG$_m$ has a molecular weight of from about 10,000 to about 30,000 Daltons.

32. A compound of claim 1 wherein $R_1$ is (D)Tyr or DesNH$_2$-Tyr, $R_2$ is Ala, and $R_3$ is Lys-PEG$_m$ wherein the PEG$_m$ has a molecular weight of from about 15,000 to about 25,000 Daltons.

33. A compound of claim 1 wherein $R_1$ is (D)Tyr or DesNH$_2$-Tyr, $R_2$ is Ala, and $R_3$ is Lys-PEG$_m$ wherein the PEG$_m$ has a molecular weight of about 20,000 Daltons.

34. A compound of claim 1 wherein $R_1$ is (D)Tyr, $R_2$ is Ala, and $R_3$ is Lys-PEG$_m$ wherein the PEG$_m$ has a molecular weight of about 20,000 Daltons.

35. A compound of claim 1 wherein selected from the group consisting of:
Ac-(D)Tyr-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 3);
DesNH$_2$-Tyr-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 4);
Ac-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 5);
DesNH$_2$-Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 6);
Ac-(D)Trp-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 7);
Ac-(D)3Pya-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 8);
Ac-2-Cl-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 9);
Ac-3-Cl-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 10);

38

Ac-4-Cl-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 11);
Ac-2-F-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 12);
Ac-3-F-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 13);
Ac-3,5-DiF-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 14);
Ac-3,4,5-TriF-(D)Phe-Ala-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Lys-NH$_2$ (SEQ ID NO: 15);
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys-NH$_2$ (SEQ ID NO: 16);
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(12,000))—NH$_2$ (SEQ ID NO: 17);
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(20,000))—NH$_2$ (SEQ ID NO: 18);
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(30,000))—NH$_2$ (SEQ ID NO: 19); and
pharmaceutically acceptable salts thereof.

36. A compound of claim 1 wherein selected from the group consisting of:
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys-NH$_2$ (SEQ ID NO: 16);
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(12,000))—NH$_2$ (SEQ ID NO: 17);
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(20,000))—NH$_2$ (SEQ ID NO: 18);
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(30,000))—NH$_2$ (SEQ ID NO: 19);
and pharmaceutically-acceptable salts thereof.

37. A compound of claim 1 wherein said compound is:
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys-NH$_2$ (SEQ ID NO: 16) or a pharmaceutically-acceptable salt thereof.

38. A compound of claim 1 wherein the compound is selected from the group consisting of:
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(12,000))—NH$_2$ (SEQ ID NO: 17);
Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val- Asn-Trp-Leu-Leu-Ala-Gln-Lys(epsilon-SSA-PEG$_m$(20,000))—NH$_2$ (SEQ ID NO: 18); and Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(30,000))—NH$_2$ (SEQ ID NO: 19);

and pharmaceutically-acceptable salts thereof.

39. A compound of claim 1 wherein the compound is selected from the group consisting of:

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(20,000))—NH$_2$ (SEQ ID NO: 18);

Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(30,000))—NH$_2$ (SEQ ID NO: 19);

and pharmaceutically-acceptable salts thereof.

40. A compound of claim 1 wherein the compound is Ac-(D)Tyr-Ala-Glu-Gly-Thr-Phe-Ile-Ser-Asp-Tyr-Ser-Ile-Ala-Met-Asp-Ala-Ile-His-Gln-Gln-Asp-Phe-Val-Asn-Trp-Leu-Leu-Ala-Gln-Lys(epsilon-SSA-PEG$_m$(20,000))—NH$_2$ (SEQ ID NO: 18) or a pharmaceutically-acceptable salt thereof.

41. A pharmaceutical composition comprising a compound according to claim 1 and a pharmaceutically acceptable carrier.

* * * * *

SEQUENCE LISTING

```
<160> NUMBER OF SEQ ID NOS: 19

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<223> OTHER INFORMATION: C-term amidated

<400> SEQUENCE: 2

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
```

```
                    20                  25                  30
```

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: D-Tyr
<220> FEATURE:
<223> OTHER INFORMATION: C-term amidated

<400> SEQUENCE: 3

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: DesNH2-Tyr
<220> FEATURE:
<223> OTHER INFORMATION: C-term amidated

<400> SEQUENCE: 4

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: D-Phe
<220> FEATURE:
<223> OTHER INFORMATION: C-term amidated

<400> SEQUENCE: 5

Phe Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 6
<211> LENGTH: 30
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: DesNH2-Phe
<220> FEATURE:
<223> OTHER INFORMATION: C-term amidated

<400> SEQUENCE: 6

Phe Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: D-Trp
<220> FEATURE:
<223> OTHER INFORMATION: C-term amidated

<400> SEQUENCE: 7

Trp Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: D-3-Pya
<220> FEATURE:
<223> OTHER INFORMATION: C-term amidated

<400> SEQUENCE: 8

Ala Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated

```
<220> FEATURE:
<221> NAME/KEY: MOD_RES
<222> LOCATION: (1)..(1)
<223> OTHER INFORMATION: 2-Cl-D-Phe
<220> FEATURE:
<223> OTHER INFORMATION: C-term amidated

<400> SEQUENCE: 9

Phe Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: 3-Cl-D-Phe
<220> FEATURE:
<223> OTHER INFORMATION: C-term amidated

<400> SEQUENCE: 10

Phe Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: 4-Cl-D-Phe
<220> FEATURE:
<223> OTHER INFORMATION: C-term amidated

<400> SEQUENCE: 11

Phe Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: 2-F-D-Phe
```

<220> FEATURE:
<223> OTHER INFORMATION: C-term amidated

<400> SEQUENCE: 12

Phe Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: 3-F-D-Phe
<220> FEATURE:
<223> OTHER INFORMATION: C-term amidated

<400> SEQUENCE: 13

Phe Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: 3,5-DiF-D-Phe
<220> FEATURE:
<223> OTHER INFORMATION: C-term amidated

<400> SEQUENCE: 14

Phe Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: 3,4,5-F3-D-Phe
<220> FEATURE:
<223> OTHER INFORMATION: C-term amidated

<400> SEQUENCE: 15

Phe Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: D-Tyr
<220> FEATURE:
<223> OTHER INFORMATION: C-term amidated

<400> SEQUENCE: 16

Tyr Ala Glu Gly Thr Phe Ile Ser Asp Tyr Ser Ile Ala Met Asp Ala
1               5                   10                  15

Ile His Gln Gln Asp Phe Val Asn Trp Leu Leu Ala Gln Lys
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (30)..(30)
<223> OTHER INFORMATION: Lys(epsilon-SSA-PEG12,000)
<220> FEATURE:
<223> OTHER INFORMATION: C-term amidated

<400> SEQUENCE: 17

Tyr Ala Glu Gly Thr Phe Ile Ser Asp Tyr Ser Ile Ala Met Asp Ala
1               5                   10                  15

Ile His Gln Gln Asp Phe Val Asn Trp Leu Leu Ala Gln Lys
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (30)..(30)
<223> OTHER INFORMATION: Lys(epsilon-SSA-PEG20,000)

```
<220> FEATURE:
<223> OTHER INFORMATION: C-term amidated

<400> SEQUENCE: 18

Tyr Ala Glu Gly Thr Phe Ile Ser Asp Tyr Ser Ile Ala Met Asp Ala
1               5                   10                  15

Ile His Gln Gln Asp Phe Val Asn Trp Leu Leu Ala Gln Lys
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (30)..(30)
<223> OTHER INFORMATION: Lys(epsilon-SSA-PEG30,000)
<220> FEATURE:
<223> OTHER INFORMATION: C-term amidated

<400> SEQUENCE: 19

Tyr Ala Glu Gly Thr Phe Ile Ser Asp Tyr Ser Ile Ala Met Asp Ala
1               5                   10                  15

Ile His Gln Gln Asp Phe Val Asn Trp Leu Leu Ala Gln Lys
            20                  25                  30
```